United States Patent
Chen

(10) Patent No.: US 10,556,875 B2
(45) Date of Patent: Feb. 11, 2020

(54) BIS-DIAZENIUMDIOLATE COMPOUNDS AS ANTI-CANCER AGENTS

(71) Applicant: ARIZONA BOARD OF REGENTS ON BEHALF OF ARIZONA STATE UNIVERSITY, Scottsdale, AZ (US)

(72) Inventor: Shengxi Chen, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/155,525

(22) Filed: Oct. 9, 2018

(65) Prior Publication Data

US 2019/0106396 A1 Apr. 11, 2019

Related U.S. Application Data

(60) Provisional application No. 62/570,502, filed on Oct. 10, 2017.

(51) Int. Cl.
| | | |
|---|---|---|
| *A61K 31/496* | (2006.01) |
| *C07D 295/30* | (2006.01) |
| *C07D 211/98* | (2006.01) |
| *A61P 35/00* | (2006.01) |

(52) U.S. Cl.
CPC ............ *C07D 295/30* (2013.01); *A61P 35/00* (2018.01); *C07D 211/98* (2013.01)

(58) Field of Classification Search
CPC .... A61K 31/496; A61K 35/00; C07D 295/30; C07D 211/98
USPC ........ 514/252.13, 150, 253.01; 544/359, 360
See application file for complete search history.

(56) References Cited

U.S. PATENT DOCUMENTS

2011/0182978 A1* 7/2011 Shami .................. A61K 9/1075
424/450

FOREIGN PATENT DOCUMENTS

WO 2017200787 A1 11/2017

OTHER PUBLICATIONS

Kiziltepe, T, et al., "JS-K, a GST-activated nitric oxide generator, induces DNAdouble-strand breaks, activates DNAdamage response pathways, and induces apoptosis in vitro and in vivo in human multiple myeloma cells", Blood 110, 709-718 (2007).
Lala, P, et al., "Role of nitric oxide in tumor progression: Lessons from experimental tumors", Cancer and Metastasis Reviews 17(1), 91-106 (1998).
Lam-Himlin, D, et al., "Malignant glioma progression and nitric oxide", Neurochemistry International 49, 764-768 (2006).
Liu, J, et al., "Nitric oxide prodrugs and metallochemotherapeutics: JS-K and CB-3-100 enhance arsenic and cisplatin cytolethality by increasing cellular accumulation", Molecular Cancer Therapeutics 3(6), 709-714 (2004).
Maciag, A, et al., "The Nitric Oxide Prodrug JS-K is Effective against Non-Small-Cell Lung Cancer Cells In Vitro and In Vivo: Involvement of Reactive Oxygen Species", Journal of Pharmacology and Experimental Therapeutics 336(2), 313-320 (2011).
Matsukado, K, et al., "Enhanced Tumor Uptake of Carboplatin and Survival in Glioma-bearing Rats by Intracarotid Infusion of Bradykinin Analog, RMP-7", Neurosurgery 39(1), 126-134 (1996).
Mitchell, J, et al., "Redox Generation of Nitric Oxide to Radiosensitize Hypoxic Cells", Int J Radiation Oncology Biol Phys 42 (4), 795-798 (1998).
Mocellin, S, et al., "Nitric Oxide, a Double Edged Sword in Cancer Biology: Searching forTherapeutic Opportunities", Med Res Rev 27(3), 317-352 (2007).
Ren, Z, et al., "JS-K, a Novel Non-Ionic Diazeniumdiolate Derivative, Inhibits Hep 3B Hepatoma Cell Growth and Induces c-Jun Phosphorylation via Multiple MAP Kinase Pathways", Journal of Cellular Physiology 197, 426-434 (2003).
Ridnour, L, et al., "Nitric oxide regulates angiogenesis through a functional switch involving thrombospondin-1", PNAS 102(37), 13147-13152 (2005).
Shami, P, et al., "Antitumor Activity of JS-K [O2-(2,4-Dinitrophenyl) 1-[(4-Ethoxycarbonyl)piperazin-1-yl]diazen-1-ium-1,2-diolate] and Related O2-Aryl Diazeniumdiolates in Vitro and in Vivo", J Med Chem 49, 4356-4366 (2006).
Shami, P, et al., "JS-K, a Glutathione/Glutathione S-Transferase-activated Nitric Oxide Donor of the Diazeniumdiolate Class with Potent Antineoplastic Activity", Molecular Cancer Therapeutics 2, 409-417 (2003).
Udupi, V, et al., "JS-K, a nitric oxide prodrug, induces cytochrome c release and caspase activation in HL-60 myeloid leukemia cells", Leukemia Research 30, 1279-1283 (2006).
Weyerbrock, A, et al., "Differential effects of nitric oxide on blood-brain barrier integrity and cerebral blood flow in Intracerebral C6 gliomas", Neuro-Oncology 13(2), 203-211 (2011).
Weyerbrock, A, et al., "JS-K, a Glutathione S-Transferase-Activated Nitric Oxide Donor With Antineoplastic Activity in Malignant Gliomas", Neurosurgery 70(2), 497-510 (2012).
Weyerbrock, A, et al., "Selective opening of the blood-tumor barrier by a nitric oxide donor and long-term survival in rats with C6 gliomas", J Neurosurg 99, 728-737 (2003).
Wink, D, et al., "Nitric Oxide and Cancer: An Introduction", Free Radical Biology & Medicinal 34(8), 951-954 (2003).
Wink, D, et al., "Nitric Oxide and Some Nitric Oxide Donor Compounds Enhance the Cytotoxicity of Cisplatin", Nitric Oxide: Biology and Chemistry 1(1), 88-94 (1997).

* cited by examiner

*Primary Examiner* — Matthew P Coughlin
*Assistant Examiner* — Sagar Patel
(74) *Attorney, Agent, or Firm* — Viksnins Harris Padys Malen LLP

(57) ABSTRACT

A series of double-component, bis O²-aryl diazeniumdiolate derivatives are provided, of which each molecule can release up to four nitric oxide molecules. These compounds show cytotoxic activities to cancer cells, such as human leukemia, breast cancer and lung cancer. Among them, the compound 3 showed the highest specific activity against human leukemia cells.

14 Claims, No Drawings

BIS-DIAZENIUMDIOLATE COMPOUNDS AS ANTI-CANCER AGENTS

CROSS REFERENCE TO RELATED APPLICATIONS

This non-provisional application claims the benefit of priority of U.S. Provisional Application Ser. No. 62/570,502 filed on 10 Oct. 2017, which is incorporated by reference in entirety.

FIELD OF THE INVENTION

A series of double-component, bis $O^2$-aryl diazeniumdiolate compounds, of which each molecule can release up to four nitric oxide molecules. These compounds showed cytotoxic activities to cancer cells, such as human leukemia, breast cancer and lung cancer. Among them, the compound 3 showed the highest specific activity to human leukemia cells.

BACKGROUND OF THE INVENTION

Nitric oxide (NO) is a signaling molecule in a number of human cells. It also involves in many physiological and pathological processes in tumor biology, regulating tumor blood flow, vascular permeability and angiogenesis, controlling the growth, migration and invasion of cancer cells. (1. Lala P K, et al, Cancer Metastasis Rev. March; 1998 17(1):91-106; Lam-Himlin D. et al, Neurochem Int. December; 2006 49(8):764-768. Epub 2006 September 2012; Mocellin S, et al, Med Res Rev. May; 2007 27(3):317-352; Ridnour L A, et al, Proc Natl Acad Sci USA. Sept. 13; 2005 102(37):13147-13152. Epub 12005 September 13142; Wink D A, et al, Free Radic Biol Med. Apr. 15; 2003 34(8):951-954). Interference of NO signaling might be a promising strategy as a novel cancer treatment. Several studies used NO to alter blood flow and vascular permeability for increasing the efficiency of drug delivery to tumors; other studies used NO to induce tumor cell killing or increase the sensitivity of chemotherapy or radiotherapy (Matsukado K, et al, Neurosurgery. 1996; 39(1):125-133; Mitchell J B, et al, International Journal of Radiation Oncology Biology Physics. 1998; 42(4):795-798; Weyerbrock A, et al, J Neurosurg. 2003; 99(4):728-737; Weyerbrock A, et al, Neuro Oncol. February; 2011 13(2):203-211; Wink D A, et al, Nitric Oxide-Biology and Chemistry. 1997; 1(1):88-94).

JS-K, [$O^2$-(2,4-dinitrophenyl) 1-[(4-ethoxycarbonyl)piperazin-1-yl]diazen-1-ium-1,2-diolate], CAS Reg. No. 205432-12-8, is a NO donor and contains a $O^2$-aryl diazeniumdiolates (NONOates) structural motif. The 2,4-dinitrophenyl group of the prodrug JS-K can be removed by a reaction with glutathione (GSH) to generate NO, which is catalyzed by glutathione-S-transferases (GSTs). (Shami P J, et al. Mol Cancer Ther. 2003; 2(4):409-417). GSTs are overexpressed in many kinds of tumors. Especially in multiple myeloma cells, GSTs are overexpressed about 7-fold comparing to normal plasma cells. The higher concentration of GSTs in tumor cells catalyzes JS-K to generate higher intracellular concentration of NO, which results in cytotoxic activities. JS-K shows a concentration-dependent and high effective antiproliferative effect to leukemia (HL-60), prostate cancer (PPC-1), multiple myeloma (MM), hepatoma (Hep 3B), and lung cancer in vitro and in vivo (Shami P J, et al, Mol Cancer Ther. 2003; 2(4):409-417; Kiziltepe T, et al. Blood. Jul. 15; 2007 110(2):709-718. Epub 2007 March 2023; Liu J, et al, Mol Cancer Ther. 2004; 3(6):709-714; Maciag A E, et al, J Pharmacol Exp Ther. February; 2011 336(2):313-320; Ren Z, et al, J Cell Physiol. 2003; 197(3): 426-434; Shami P J, et al, J Med Chem. Jul. 13; 2006 49(14):4356-4366; Udupi V, et al, Leuk Res. October; 2006 30(10):1279-1283. Epub 2006 January 1224).

The mechanisms of inducing cell death by JS-K includes arylation of GSH; activation of caspases-3, -8 and -9; induction of protein kinases p38, JNK and (MAPK) ERK; and other cellular nucleophiles (Ren Z, et al, J Cell Physiol. 2003; 197(3):426-434; Shami P J, et al, J Med Chem. Jul. 13; 2006 49(14):4356-4366). In leukemia cells, JS-K also induces mitochondrial cytochrome c release (Udupi V, et al, Leuk Res. October; 2006 30(10):1279-1283. Epub 2006 January 1224).

Bis $O^2$-aryl diazeniumdiolate compounds with optimized properties may have increased efficacy in treating hyperproliferative disorders, including cancer. Therefore, there is a need for new compounds to treat cancer, especially pancreatic cancer.

SUMMARY OF THE INVENTION

The invention provides compounds that treat cancer and other hyperproliferative disorders and includes bis $O^2$-aryl diazeniumdiolate compounds selected from formula I:

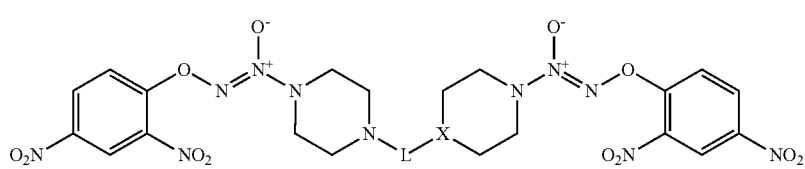

wherein:

X is CH or N; and

L is selected from $C_1$-$C_{10}$ alkyldiyl, $C_1$-$C_{10}$ alkyldiyl-($C_3$-$C_6$ cycloalkyldiyl), and $C_1$-$C_{10}$ alkyldiyl-($C_3$-$C_6$ cycloalkyldiyl)-$C_1$-$C_{10}$ alkyldiyl, where alkyldiyl and cycloalkyldiyl are independently and optionally substituted with one or more groups selected from halo, hydroxy, nitro, cyano, ($C_1$-$C_6$)alkoxy, and oxo (=O);

or a pharmaceutically-acceptable salt thereof.

The invention also provides a pharmaceutical composition comprising a compound of formula I, or a pharmaceutically acceptable salt thereof, and a pharmaceutically acceptable carrier, glidant, or excipient.

The invention also provides a method for treating cancer in an animal, comprising administering a therapeutically-effective amount of a compound of formula I, or a pharmaceutically acceptable salt thereof, to the animal. The cancer to be treated is selected from pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors. In one embodiment, the cancer is breast cancer.

The invention also provides a method for inhibiting cancer cell growth in an animal comprising administering an inhibitory effective amount of a compound of formula I, or a pharmaceutically acceptable salt thereof, to the animal. In one embodiment, the cancer cell is a breast cancer cell.

The invention also provides processes and intermediates disclosed herein that are useful for preparing a compound of formula I or a salt thereof.

DEFINITIONS

The term "alkyldiyl" by itself or as part of another substituent means a divalent radical derived from an alkane (including straight and branched alkanes), as exemplified by —$CH_2$—, —$CH_2CH_2$—, and —$CH_2CH_2CH_2$—. Alkyldiyl groups may be optionally substituted with one or more groups selected from halo, hydroxy, nitro, cyano, ($C_1$-$C_6$) alkoxy, and oxo (=O)

The term "cycloalkyldiyl" by itself or as part of another substituent means a divalent radical derived from an cycloalkyl (including straight and branched alkanes), as exemplified by cyclopropyldiyl, cyclobutyldiyl, cyclopentyldiyl, 1-cyclopent-1-enyldiyl, 1-cyclopent-2-enyldiyl, 1-cyclopent-3-enyldiyl, cyclohexyldiyl, 1-cyclohex-1-enyldiyl, 1-cyclohex-2-enyldiyl, 1-cyclohex-3-enyldiyl and cycloheptyldiyl. Cycloalkyldiyl divalent radicals include those derived from a single saturated (i.e., cycloalkyl) or a single partially unsaturated (e.g., cycloalkenyl, cycloalkadienyl, etc.) ring having 3 to 7 carbon atoms (i.e. ($C_3$-$C_7$) cycloalkyl). The term "cycloalkyl" also include multiple condensed ring systems (e.g. ring systems comprising 2, 3 or 4 carbocyclic rings). Accordingly, cycloalkyl includes multicyclic cycloalkyls having 7 to 12 carbon atoms as a bicycle, and up to about 20 carbon atoms as a polycycle. Multicyclic cycloalkyl groups can be connected to each other via a single carbon atom to form a spiro connection (e.g. spiropentane, spiro[4,5]decane, spiro[4.5]decane), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane). Cycloalkyldiyl groups may be optionally substituted with one or more groups selected from halo, hydroxy, nitro, cyano, ($C_1$-$C_6$) alkoxy, and oxo (=O)

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers (stereocenters), and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

DETAILED DESCRIPTION OF EXEMPLARY EMBODIMENTS

JS-K is activated by glutathione S-transferase (GST) for nitric oxide (NO) releasing, which is a part of the mechanism of its anticancer activity. The delivery efficiency of nitric oxide may be increased or otherwise optimized by linking two parts of JS-K together in a compound having formula I:

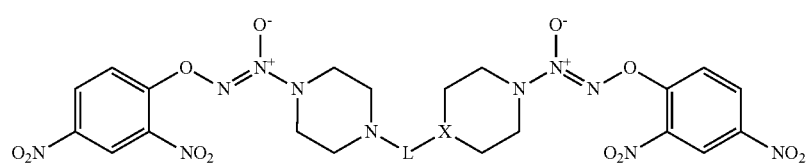

wherein:

X is CH or N; and

L is selected from $C_1$-$C_{10}$ alkyldiyl, $C_1$-$C_{10}$ alkyldiyl-($C_3$-$C_6$ cycloalkyldiyl), and $C_1$-$C_{10}$ alkyldiyl-($C_3$-$C_6$ cycloalkyldiyl)-$C_1$-$C_{10}$ alkyldiyl, where alkyldiyl and cycloalkyldiyl are independently and optionally substituted with one or more groups selected from halo, hydroxy, nitro, cyano, ($C_1$-$C_6$) alkoxy, and oxo (=O);

or a pharmaceutically-acceptable salt thereof.

Exemplary embodiments of a formula I compound include formulae Ia, Ib, or Ic:

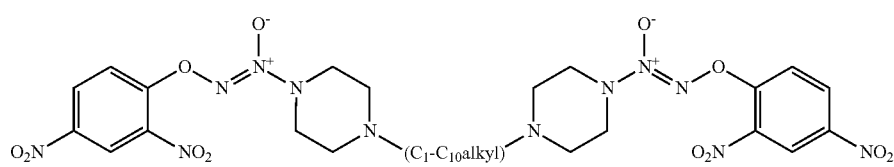

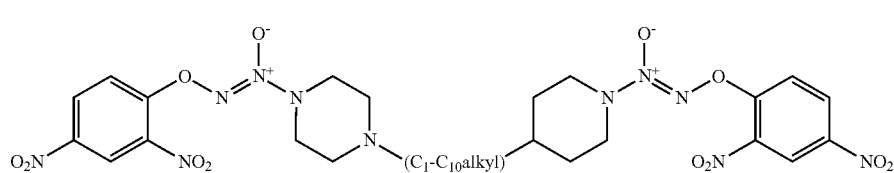

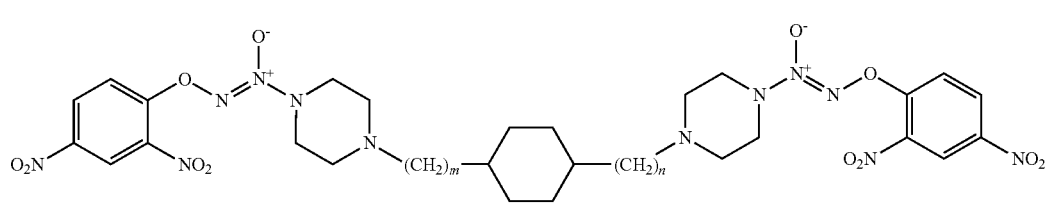

where m and n are independently selected from 1, 2, and 3.

In one exemplary embodiment, X is CH.
In one exemplary embodiment, X is N.
In one exemplary embodiment, L is optionally substituted $C_1$-$C_{10}$ alkyldiyl.
In one exemplary embodiment, L is selected from —$CH_2$—, —$CH_2CH_2$—, and —$CH_2CH_2CH_2$—.
In one exemplary embodiment, L is optionally substituted $C_1$-$C_{10}$ alkyldiyl-($C_3$-$C_6$ cycloalkyldiyl).
In one exemplary embodiment, L is optionally substituted $C_1$-$C_{10}$ alkyldiyl-($C_3$-$C_6$ cycloalkyldiyl)-$C_1$-$C_{10}$ alkyldiyl.

Preparation of Bis-Diazeniumdiolate Compounds of Formula I

Formula I compounds were prepared by the methods, processes, intermediates, reactions, and reagents in Schemes 1-3 and the Examples. Two molecules of JS-K were coupled via an alkane linker in an exemplary method to synthesize the formula I, double-component, bis $O^2$-aryl diazeniumdiolate compounds. A series of bis $O^2$-aryl diazeniumdiolate compounds were designed and synthesized and their anti-cancer activities tested, including compounds 1-4:

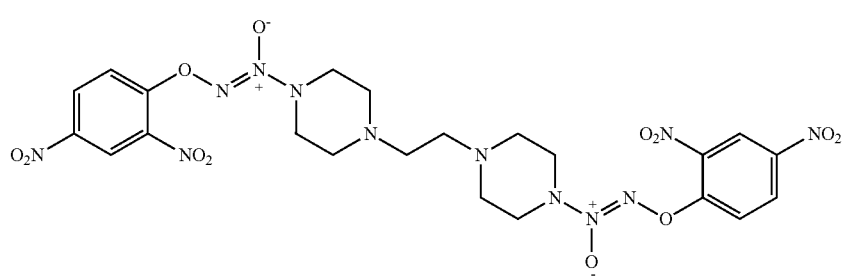

1

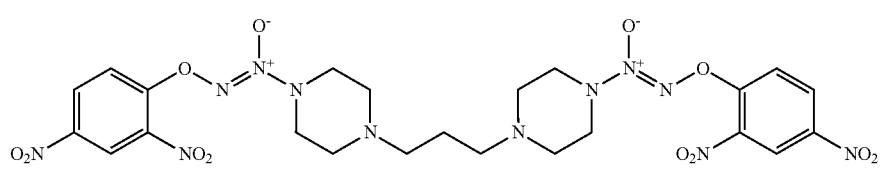

2

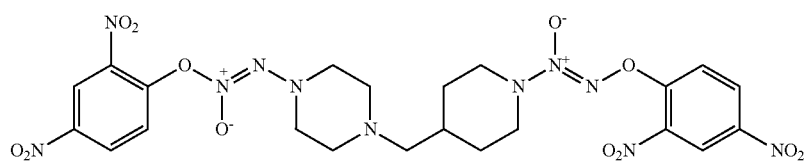

3

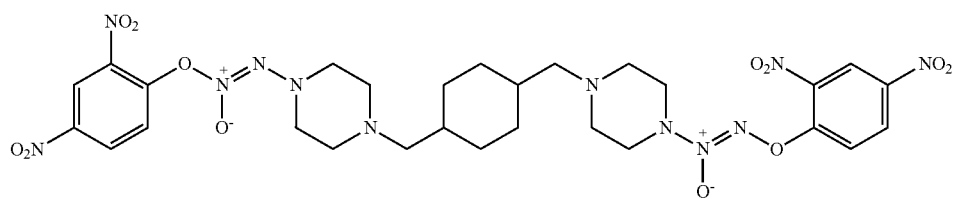

4

Scheme 1

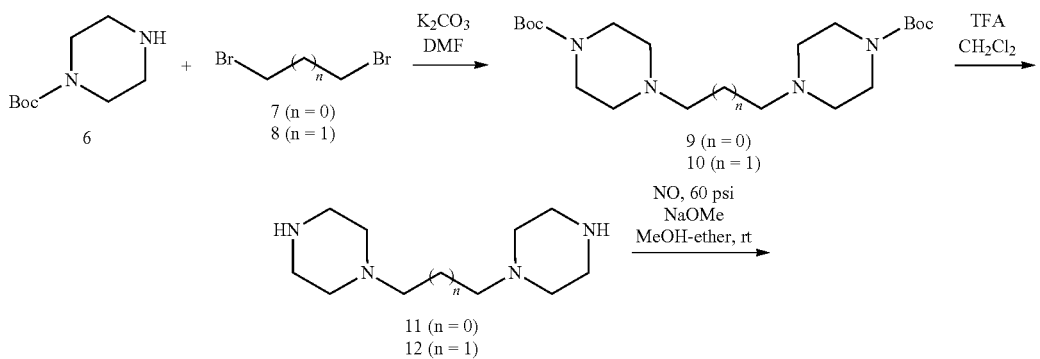

-continued

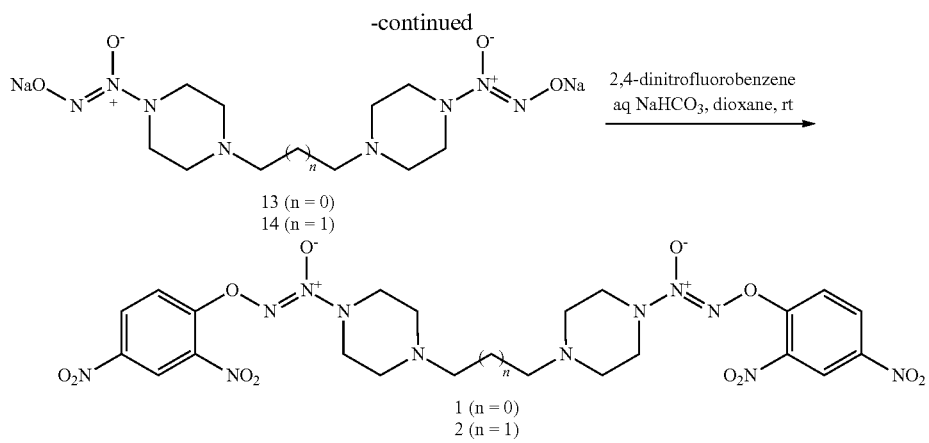

13 (n = 0)
14 (n = 1)

1 (n = 0)
2 (n = 1)

As shown in Scheme 1, tert-butyl piperazine-1-carboxylate 6 reacted with 1,2-dibromoethane (7) or 1,3-dibromopropane (8) to obtain compounds di-tert-butyl 4,4'-(ethane-1,3-diyl)bis(piperazine-1-carboxylate) 9 and di-tert-butyl 4,4'-(propane-1,3-diyl)bis(piperazine-1-carboxylate) 10 with a yield of 43% and 78%, respectively. The BOC-protection groups were removed by trifluoroacetic acid (TFA) to generate the intermediates 1,2-di(piperazin-1-yl)ethane 11 and 1,3-di(piperazin-1-yl)propane 12, which were treated with nitric oxide gas to obtain the intermediates disodium (1Z,1'Z)-1,1'-(ethane-1,2-diylbis(piperazine-4,1-diyl))bis(2-(11-oxidaneyl)diazene 1-oxide) 13 and disodium (1Z,1'Z)-1,1'-(propane-1,3-diylbis(piperazine-4,1-diyl))bis(2-(11-oxidaneyl)diazene 1-oxide) 14, respectively. The intermediates 13 and 14 were reacted with 2,4-dinitrofluorobenzene to obtain (1Z,1'Z)-1,1'-(ethane-1,2-diylbis(piperazine-4,1-diyl))bis(2-(2,4-dinitrophenoxy)diazene 1-oxide) 1 and (1Z,1'Z)-1,1'-(propane-1,3-diylbis(piperazine-4,1-diyl))bis(2-(2,4-dinitrophenoxy)diazene 1-oxide) 2 in a final yield of 10% and 17%, respectively, after three steps of reaction.

Scheme 2

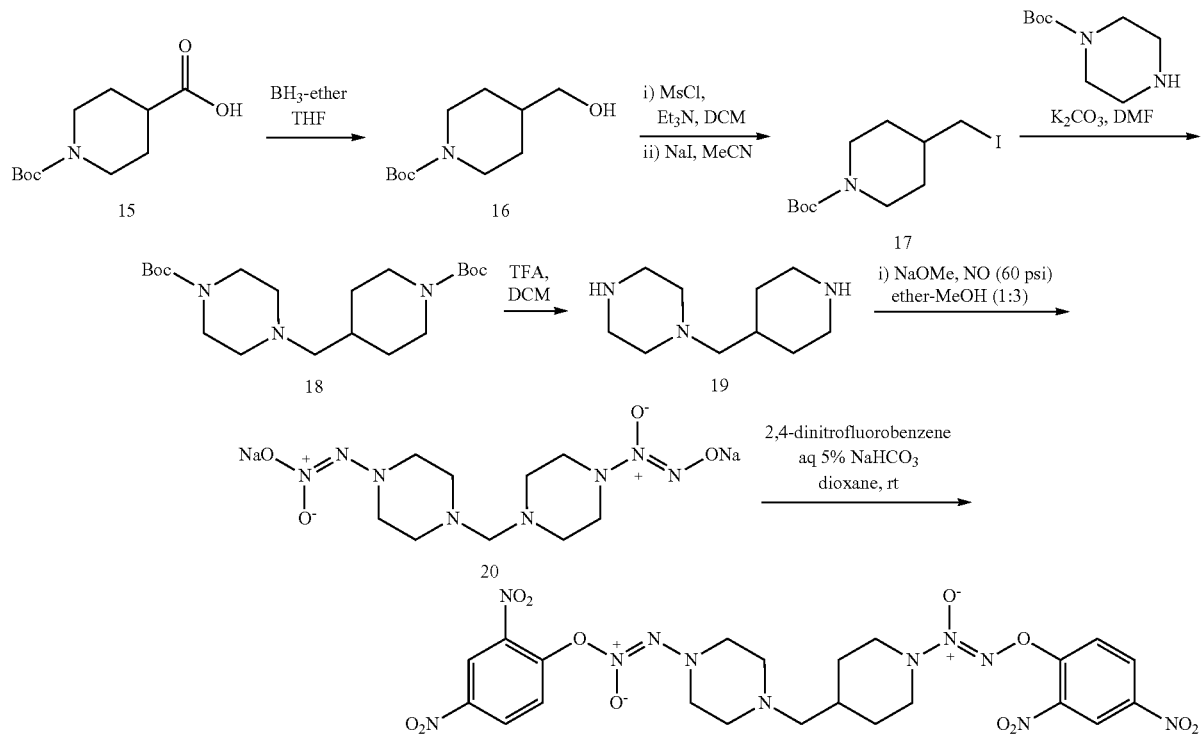

The synthesis of compound 3 was described as shown in Scheme 2. Commercially available, 1-(tert-butoxycarbonyl)piperidine-4-carboxylic acid 15 was treated with $BH_3$ to obtain tert-butyl 4-(hydroxymethyl)piperidine-1-carboxylate 16 in a yield of 93% and which was reacted with NaI to generate tert-butyl 4-(iodomethyl)piperidine-1-carboxylate 17 in a yield of 50%. Intermediate 17 was coupled with tert-butyl piperazine-1-carboxylate 6 to obtain tert-butyl 4-((1-(tert-butoxycarbonyl)piperidin-4-yl)methyl)piperazine-1-carboxylate 18 in a yield of 66%. The BOC-protection groups of 18 were removed by trifluoroacetic acid (TFA) to generate 1-(piperidin-4-ylmethyl)piperazine 19, which was treated with nitric oxide gas to obtain disodium (Z)-2-(4-((1-(2-(11-oxidaneyl)-1-oxidodiazen-1-yl)piperidin-4-yl)methyl)piperazin-1-yl)-1-(11-oxidaneyl)diazene 1-oxide 20. Intermediate 20 was reacted with 2,4-dinitrofluorobenzene to obtain (E)-1-(2,4-dinitrophenoxy)-2-(4-((1-((Z)-2-(2,4-dinitrophenoxy) 1-oxidodiazen-1-yl)piperidin-4-yl)methyl)piperazin-1-yl)diazene 1-oxide 3 in a final yield of 7.9% after three steps of reaction.

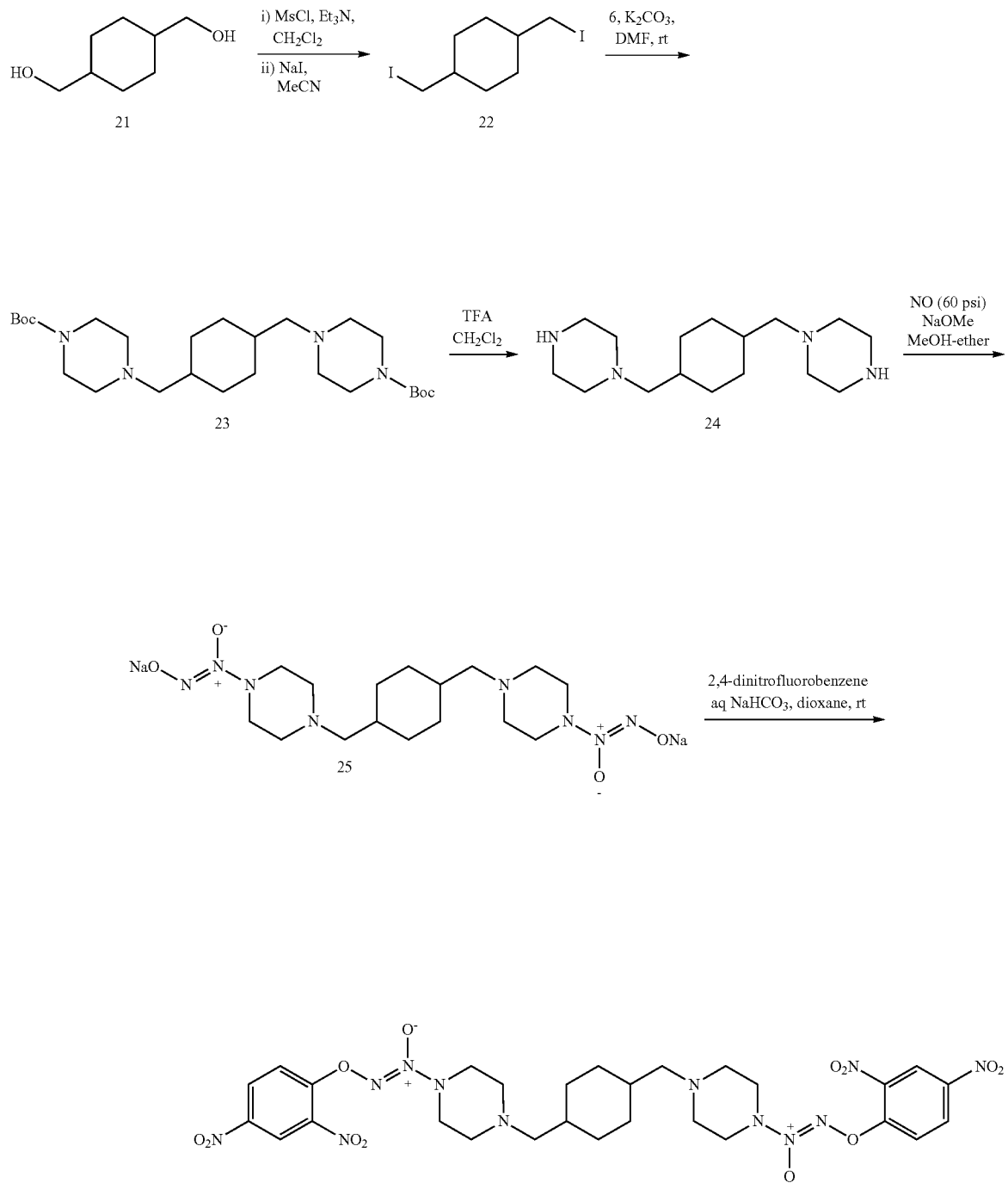

As shown in Scheme 3, the compound 4 was synthesized using a similar procedure as Schemes 1 and 2. Cyclohexane-1,4-diyldimethanol 21 is bis-mesylated with methanesulfonyl chloride in trimethylamine and dichloromethane followed by displacement with iodine by sodium iodide in acetonitrile to give 1,4-bis(iodomethyl)cyclohexane 22. Intermediate 22 was reacted with tert-butyl piperazine-1-carboxylate 6 and potassium carbonate in dimethylformamide at room temperature to give di-tert-butyl 4,4'-(cyclohexane-1,4-diylbis(methylene))bis(piperazine-1-carboxylate) 23. Removal of the Boc groups from 23 with trifluoroacetic acid in dichloromethane gave 1,4-bis(piperazin-1-ylmethyl)cyclohexane 24. Treatment of 24 with nitric oxide gas, sodium methoxide in methanol and ether gave disodium (1Z,1'Z)-1,1'-((cyclohexane-1,4-diylbis(methylene))bis(piperazine-4,1-diyl))bis(2-(11-oxidaneyl)diazene 1-oxide) 25. Intermediate 25 was reacted with 2,4-dinitrofluorobenzene in aqueous sodium bicarbonate to give (1Z,1'Z)-1,1'-((cyclohexane-1,4-diylbis(methylene))bis(piperazine-4,1-diyl))bis(2-(2,4-dinitrophenoxy)diazene 1-oxide) 4.

(101 mg, 0.54 mmol) of 1,2-dibromoethane 7 and 592 mg (4.28 mmol) of $K_2CO_3$ at room temperature. After 24 h, reaction mixture was diluted with 25 mL of water and extracted with two 50 mL portions of ethyl acetate. The organic phase was dried ($MgSO_4$) and concentrated under diminished pressure. The residue was purified by chromatography on a silica gel column (10×2 cm). Elution with 19:1 ethyl acetate/methanol gave desired product 9 as a colorless solid: yield 183 mg (43%); silica gel TLC $R_f$ 0.27 (9:1 ethyl acetate/methanol); $^1$H NMR ($CDCl_3$) δ 1.47 (s, 18H), 2.33-2.40 (m, 12H) and 3.37-3.45 (m, 8H); $^{13}$C NMR ($CDCl_3$) δ 28.6, 53.5, 53.6, 56.1, 79.8 and 154.9.

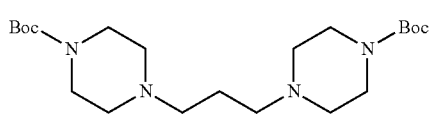

TABLE 1

Half maximal inhibitory concentration ($IC_{50}$) of compounds 1-4 against different cancer cells.

| Cell line | Half maximal inhibitory concentration (IC50, µmol/L) | | | | |
|---|---|---|---|---|---|
| | Compound 1 | Compound 2 | Compound 3 | Compound 4 | JS-K |
| CCRF-CEM | 2.64 ± 0.37 | 3.73 ± 0.15 | 0.46 ± 0.02 | 2.54 ± 0.14 | 0.29 ± 0.01 |
| Jurkat E6-1 | 3.71 ± 0.04 | 4.06 ± 0.18 | 1.94 ± 0.08 | 3.01 ± 0.22 | 0.52 ± 0.02 |
| BT474 | 10.7 ± 0.97 | 10.8 ± 0.08 | 7.06 ± 1.03 | 6.01 ± 0.21 | 3.66 ± 0.41 |
| A549 | 17.1 ± 1.02 | 18.8 ± 0.21 | 11.3 ± 1.61 | 18.5 ± 0.15 | 2.11 ± 0.15 |
| MDA-MB-231 | 17.6 ± 0.08 | >20 | 17.86 ± 1.01 | 16.4 ± 0.53 | 7.93 ± 0.47 |

As shown in Table 1, the control compound JS-K had a high inhibitory effect on cellular proliferation against all four tested cancer cells including, breast cancer cell BT474, breast cancer cell MDA-MB-231, lung cancer cell A549, leukemia cell CCRF-CEM and leukemia Jurkat cells. The compounds of the invention 1-4 had comparable activity to JS-K against all these five tested cancer cells. Among them, the compound 3 showed higher selectivity than JS-K. It had a similar $IC_{50}$ to JS-K against leukemia CEM cells (0.46 µM: 0.29 µM). However, the $IC_{50}$ values for compound 3 against other four cancer cells were 1.9-5.4 fold higher (less cell killing potency) than for JS-K. Especially, it showed less efficiency to breast cancer and lung cancer. Compound 3 had a higher selectivity to leukemia cells than to breast cancer and lung cancer cells.

EXAMPLES

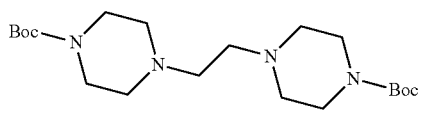 [SMILES: CC(C)(C)OC(=O)N1CCN(CCN2CCN(C(=O)OC(C)(C)C)CC2)CC1]

Di-tert-butyl 4,4'-(ethane-1,2-diyl)bis(piperazine-1-carboxylate) 9

To a stirred solution of 200 mg (1.07 mmol) of mono Boc-piperazine 6 in 5 mL of dry DMF were added 47.0 µL Di-tert-butyl 4,4'-(propane-1,3-diyl)bis(piperazine-1-carboxylate) 10

To a stirred solution of 300 mg (1.61 mmol) of mono Boc-piperazine 6 in 5 mL of dry DMF were added 82.0 µL (163 mg, 0.80 mmol) of 1,3-dibromopropane 8 and 890 mg (6.44 mmol) of $K_2CO_3$ at room temperature. After 24 h, reaction mixture was diluted with 25 mL of water and extracted with two 50 mL portions of ethyl acetate. The organic phase was dried ($MgSO_4$) and concentrated under diminished pressure. The residue was purified by chromatography on a silica gel column (10×2 cm). Elution with 19:1 ethyl acetate/methanol gave desired product 10 as a colorless solid: yield 521 g (78%); silica gel TLC $R_f$ 0.27 (9:1 ethyl acetate/methanol); $^1$H NMR ($CDCl_3$) δ 1.46 (s, 18H), 1.64-1.74 (m, 2H), 2.35-2.39 (m, 12H) and 3.41-3.44 (m, 8H); $^{13}$C NMR ($CDCl_3$) δ 28.4, 31.4, 36.4, 53.1, 56.6, 79.5 and 154.7.

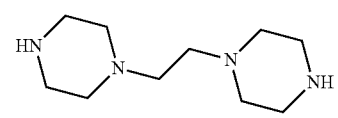 [SMILES: C1CN(CCN2CCNCC2)CCN1]

1,2-Di(piperazin-1-yl)ethane 11

To a solution of 50 mg (0.13 mmol) of 9 in 500 µL of $CH_2Cl_2$ was added 500 µL of $CF_3COOH$. The reaction mixture was stirred overnight and then concentrated under diminished pressure to obtain the deprotected amine, which was used in next step without further purification.

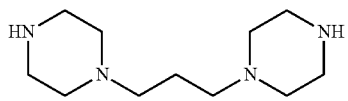 [SMILES: C(CN1CCNCC1)CN1CCNCC1]

1,3-Di(piperazin-1-yl)propane 12

To a solution of 100 mg (0.24 mmol) of 10 in 500 μL of CH₂Cl₂ was added 500 μL of CF₃COOH. The reaction mixture was stirred overnight and then concentrated under diminished pressure to obtain the deprotected amine, which was used in next step without further purification.

(1Z,1'Z)-1,1'-(propane-1,3-diylbis(piperazine-4,1-diyl))bis(2-(2,4-dinitrophenoxy)diazene 1-oxide) 2

To a stirred solution of 51.5 mg (0.24 mmol) amine 12 in 15 mL of 1:3 methanol-diethyl ether was added 0.72 mL (0.72 mmol) of 1M sodium methoxide (NaOMe) solution in a Parr bottle at room temperature. The reaction mixture was charged with 60 psi of nitric oxide and stirred at room temperature for 24 h. The white crystalline solid was collected by filtration and washed with diethyl ether and dried under vacuum.

To an ice-cooled solution of 14 in 1 mL of aqueous 5% NaHCO₃ solution was added a solution of 89.3 mg (0.48 mmol) of 2,4-dinitrofluorobenzene in 1 mL of 1,4-dioxane.

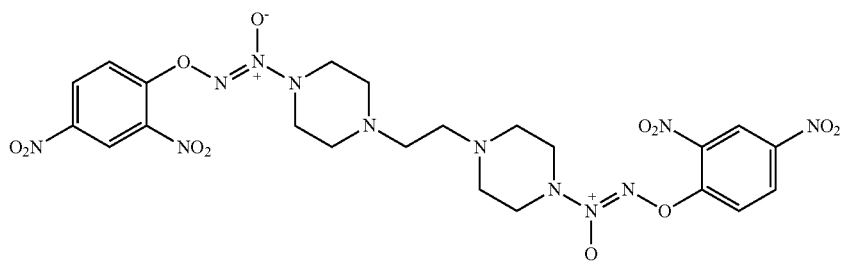

1

(1Z,1'Z)-1,1'-(ethane-1,2-diylbis(piperazine-4,1-diyl))bis(2-(2,4-dinitrophenoxy)diazene 1-oxide) 1

To a stirred solution of 25.0 mg (0.13 mmol) of amine 11 in 15 mL of 1:3 methanol-diethyl ether was added 0.38 mL (0.38 mmol) of 1M NaOMe solution in Parr bottle at room temperature. The reaction mixture was charged with 60 psi of nitric oxide and stirred at room temperature for 24 h. The white crystalline solid was collected by filtration and washed with diethyl ether and dried under vacuum.

To an ice-cooled solution of 13 in 1 mL of aqueous 5% NaHCO₃ solution was added a solution of 47.0 mg (0.25 mmol) of 2,4-dinitrofluorobenzene in 1 mL of 1,4-dioxane. The reaction mixture was allowed to ambient temperatures and stirred for overnight. The reaction mixture was diluted with 5 mL of water and extracted with two 10 mL portions of ethyl acetate. The organic phase was dried (MgSO₄) and concentrated under diminished pressure. The residue was purified by chromatography on a silica gel column (10×1 cm). Elution with 15:1 ethyl acetate/methanol gave desired product 1 as a pale yellow solid: yield 8.0 mg (10%); silica gel TLC $R_f$ 0.19 (9:1 ethyl acetate/methanol); ¹H NMR (DMSO-d₆) δ 2.33-2.38 (m, 12H) and 3.46-3.54 (m, 8H), 7.68 (d, 2H, J=8.8 Hz), 8.47 (dd, 2H, J=8.8 Hz and 2.4 Hz) and 8.87 (d, 2H, J=2.4 Hz); ¹³C NMR (DMSO-d₆) δ 52.1, 53.6, 55.3, 117.7, 122.2, 129.2, 137.3, 142.3 and 153.9.

The reaction mixture was allowed to ambient temperatures and stirred for overnight. The reaction mixture was diluted with 5 mL of water and extracted with two 10 mL portions of ethyl acetate. The organic phase was dried (MgSO₄) and concentrated under diminished pressure. The residue was purified by chromatography on a silica gel column (10×1 cm). Elution with 15:1 ethyl acetate/methanol gave desired product 2 as a pale yellow solid: yield 28 mg (17%); silica gel TLC $R_f$ 0.19 (9:1 ethyl acetate/methanol); ¹H NMR (DMSO-d₆) δ 1.65-1.74 (m, 2H), 2.32-2.38 (m, 12H) and 3.44-3.51 (m, 8H), 7.69 (d, 2H, J=9.2 Hz), 8.47 (dd, 2H, J=9.2 Hz and 2.4 Hz) and 8.88 (d, 2H, J=2.4 Hz); ¹H NMR (DMSO-d₆) δ 31.3, 36.5, 52.7, 56.5, 117.5, 122.2, 129.3, 137.4, 142.1 and 153.9.

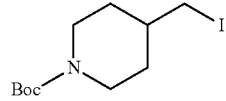

tert-Butyl 4-(Iodomethyl)piperidine-1-carboxylate 17

The compound 16 was prepared using compound 15 as starting material in a yield of 93%. To an ice-cooled stirred

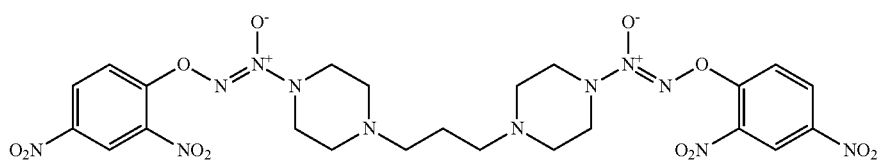

2 solution of 400 mg (1.86 mmol) of compound 16 in 5 mL of CH$_2$Cl$_2$ was added 0.52 mL (375 mg, 3.72 mmol) of triethylamine and 0.17 mL (256 mg, 2.23 mmol) of methanesulfonyl chloride. The reaction mixture was allowed to warm to ambient temperature and stirred for 2 h. The reaction mixture was diluted with 35 mL of CH$_2$Cl$_2$, washed successively with 20 mL of water, 20 mL of satd. aq. NaHCO$_3$, 20 mL of brine, dried (MgSO$_4$) and concentrated under reduced pressure. The resulting crude product was dissolved in 2 mL of acetonitrile and 1.39 g (9.30 mmol) of NaI was added. The reaction mixture was stirred at r.t. for 12 h, and poured into 50 mL of water, extracted with two 30-mL portions of ethyl acetate. The combined organic extract was washed with 20 mL of brine, dried (MgSO$_4$) and concentrated under diminished pressure. The residue was purified by flash chromatography on a silica gel column (15×2 cm). Elution with 2:3 hexanes-ethyl acetate afforded 17 as a colorless solid: yield 302 mg (50%); silica gel TLC R$_f$ 0.31 (2:3 hexanes-ethyl acetate); $^1$H NMR (CDCl$_3$) δ 1.11-1.19 (m, 2H), 1.45 (s, 9H), 1.59-1.62 (m, 1H), 1.82 (d, 2H, J=13.2 Hz), 2.66 (brs, 2H), 3.12 (d, 2H, J=6.8 Hz) and 4.10 (brs, 2H); $^{13}$C NMR (CDCl$_3$) δ 13.5, 28.4, 32.5, 38.4, 43.5, 79.3 and 154.5.

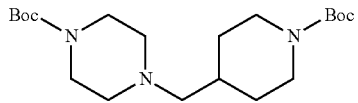 [SMILES: CC(C)(C)OC(=O)N1CCC(CN2CCN(C(=O)OC(C)(C)C)CC2)CC1]

tert-Butyl 4-((1-(tert-Butoxycarbonyl)piperidin-4-yl) methyl)piperazine-1-carboxylate 18

To a stirred solution of 250 mg (0.77 mmol) of 17 in 2 mL of anhydrous DMF was added 319 mg (2.31 mmol) of K$_2$CO$_3$ followed by 0.14 mL (0.77 mmol) of boc-piperazine 25 at r.t. After 15 h, the reaction mixture was poured into 50 mL of water and extracted with three 30-mL portions of ethyl acetate. The combined organic extract was washed with 40 mL of brine, dried (MgSO$_4$) and concentrated under diminished pressure. The residue was purified by flash chromatography on a silica gel column (15×2 cm). Elution with 1:1 hexanes-EtOAc afforded 18 as a colorless solid: yield 194 mg (66%); silica gel TLC R$_f$ 0.36 (1:1 hexanes-EtOAc); $^1$H NMR (CDCl$_3$) δ 1.01-1.11 (m, 2H), 1.452 (s, 9H), 1.456 (s, 9H), 1.59-1.67 (m, 1H), 1.73 (d, 2H, J=13.6 Hz), 2.17 (d, 2H, J=7.2 Hz), 2.33 (t, 4H, J=4.8 Hz), 2.68 (t, 2H, J=11.6 Hz), 3.40 (t, 4H, J=4.8 Hz) and 4.09 (brs, 2H); $^{13}$C NMR (CDCl$_3$) δ 28.30, 28.34, 30.6, 33.4, 43.6, 43.8, 53.3, 64.4, 79.0, 79.2, 154.6 and 154.7.

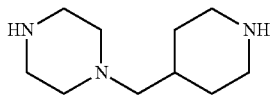

1-(Piperidin-4-ylmethyl)piperazine 19

To a solution of 152 mg (0.40 mmol) of 18 in 500 μL of CH$_2$Cl$_2$ was added 500 μL of CF$_3$COOH. The reaction mixture was stirred overnight and then concentrated under diminished pressure to obtain the deprotected amine, which was used in next step without further purification.

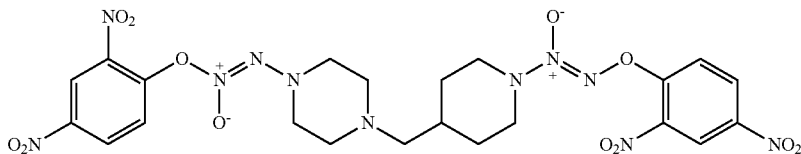

(E)-1-(2,4-dinitrophenoxy)-2-(4-((1-((Z)-2-(2,4-dinitrophenoxy)-1-oxidodiazen-1-yl)piperidin-4-yl) methyl)piperazin-1-yl)diazene 1-oxide 3

To a stirred solution of 100 mg (0.40 mmol) of amine 19 in 15 mL of 1:3 methanol-diethyl ether was added 1.19 mL (1.19 mmol) of 1M NaOMe solution in Parr bottle at room temperature. The reaction mixture was charged with 60 psi of nitric oxide and stirred at room temperature for 24 h. The white crystalline solid of 20 was collected by filtration and washed with diethyl ether and dried under vacuum.

To an ice-cooled solution of the above obtained solid in 1 mL of aqueous 5% NaHCO$_3$ solution was added a solution of 47.0 mg (0.25 mmol) of 2,4-dinitrofluorobenzene in 1 mL of 1,4-dioxane. The reaction mixture was allowed to ambient temperatures and stirred for overnight. The reaction mixture was diluted with 5 mL of water and extracted with two 10 mL portions of ethyl acetate. The organic phase was dried (MgSO$_4$) and concentrated under diminished pressure. The residue was purified by chromatography on a silica gel column (10×1 cm). Elution with 15:1 ethyl acetate/methanol gave desired product 3 as a colorless solid: yield 7.2 mg (7.9%); silica gel TLC R$_f$ 0.19 (2:1 ethyl acetate/hexanes); $^1$H NMR (DMSO-d$_6$) δ 1.01-1.10 (m, 2H), 1.59-1.69 (m, 1H), 1.77 (d, 2H, J=12.4 Hz), 2.17 (d, 2H, J=6.8 Hz), 2.30 (t, 4H, J=4.8 Hz), 2.67 (t, 2H, J=11.6 Hz), 3.44 (t, 4H, J=4.8 Hz), 4.06 (brs, 2H), 7.63 (d, 1H, J=8.4 Hz), 7.65 (d, 1H, J=8.8 Hz), 7.40-7.46 (m, 2H), 8.83 (d, 1H, J=2.4 Hz) and 8.85 (d, 1H, J=2.8 Hz); $^{13}$C NMR (CDCl$_3$) δ 30.5, 33.4, 43.1, 43.9, 53.8, 64.3, 169.8, 117.2, 122.2, 122.3, 129.3, 129.6, 136.8, 136.9, 141.4, 141.7, 154.5 and 154.7.

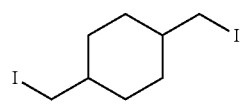

1,4-Bis(iodomethyl)cyclohexane 22

To an ice-cooled stirred solution of 500 mg (1.86 mmol) of compound 21 in 10 mL of CH$_2$Cl$_2$ was added 1.20 mL (875 mg, 8.67 mmol) of triethylamine and 0.32 mL (477 mg, 4.16 mmol) of methanesulfonyl chloride. The reaction mixture was allowed to warm to ambient temperature and stirred for 2 h. The reaction mixture was diluted with 35 mL of CH$_2$Cl$_2$, washed successively with 20 mL of water, 20 mL of satd. aq. NaHCO$_3$, 20 mL of brine, dried (MgSO$_4$) and concentrated under reduced pressure. The resulting crude product was dissolved in 2 mL of acetonitrile and 2.60 g (17.3 mmol) of NaI was added. The reaction mixture was stirred at r.t. for 12 h, and poured into 50 mL of water, extracted with two 30-mL portions of ethyl acetate. The 1,4-Bis(piperazin-1-ylmethyl)cyclohexane 24

To a solution of 200 mg (0.42 mmol) of 23 in 500 μL of CH$_2$Cl$_2$ was added 500 μL of CF$_3$COOH. The reaction mixture was stirred overnight and then concentrated under diminished pressure to obtain the deprotected amine, which was used in next step without further purification.

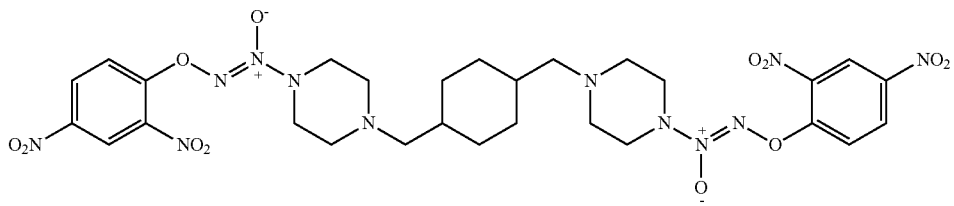

4 combined organic extract was washed with 20 mL of brine, dried (MgSO$_4$) and concentrated under diminished pressure. The residue was purified by flash chromatography on a silica gel column (15×2 cm). Elution with 1:4 hexanes-ethyl acetate afforded 22 as a colorless liquid: yield 706 mg (56%); silica gel TLC R$_f$ 0.43 (3:2 hexanes-ethyl acetate); $^1$H NMR (CDCl$_3$) δ 1.45-1.54 (m, 4H), 1.57-1.67 (m, 4H), 1.70-1.75 (m, 2H) and 3.20 (d, 2H, J=7.2 Hz); $^{13}$C NMR (CDCl$_3$) δ 13.2, 28.6 and 37.9.

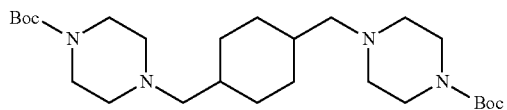 [SMILES: CC(C)(C)OC(=O)N1CCN(CC2CCC(CN3CCN(C(=O)OC(C)(C)C)CC3)CC2)CC1]

Di-tert-butyl 4,4'-(cyclohexane-1,4-diylbis(methylene))bis(piperazine-1-carboxylate) 23

To a stirred solution of 320 mg (0.88 mmol) of 22 in 2 mL of anhydrous DMF was added 486 mg (3.52 mmol) of K$_2$CO$_3$ followed by 327 mg (1.76 mmol) of 6 at r.t. After 15 h, the reaction mixture was poured into 50 mL of water and extracted with three 30-mL portions of ethyl acetate. The combined organic extract was washed with 40 mL of brine, dried (MgSO$_4$) and concentrated under diminished pressure. The residue was purified by flash chromatography on a silica gel column (15×2 cm). Elution with 1:1 hexanes-EtOAc afforded 23 as a colorless liquid: yield 317 mg (75%); silica gel TLC R$_f$ 0.22 (1:1 hexanes-EtOAc); $^1$H NMR (CDCl$_3$) δ 1.29-1.36 (m, 4H), 1.46-1.51 (m, 4H), 1.69 (m, 2H), 2.20 (d, 4H, J=7.6 Hz), 2.31 (t, 8H, J=4.0 Hz) and 3.40 (t, 8H, J=2.6 Hz); $^{13}$C NMR (CDCl$_3$) δ 27.1, 28.4, 31.4, 32.3, 53.4, 62.5, 79.2 and 154.6.

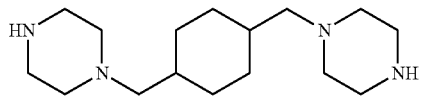 [SMILES: C1CN(CC2CCC(CN3CCNCC3)CC2)CCN1]

(1Z,1'Z)-1,1'-((cyclohexane-1,4-diylbis(methylene))bis(piperazine-4,1-diyl))bis(2-(2,4-dinitrophenoxy)diazene 1-oxide) 4

To a stirred solution of 85 mg (0.30 mmol) of amine 24 in 15 mL of 1:3 methanol-diethyl ether was added 0.91 mL (0.91 mmol) of 1M NaOMe solution in Parr bottle at room temperature. The reaction mixture was charged with 60 psi of nitric oxide and stirred at room temperature for 24 h. The white crystalline solid was collected by filtration and washed with diethyl ether and dried under vacuum; yield 21.3 mg (16%).

To an ice-cooled solution of 21.3 mg (0.05 mmol) of 25 in 1 mL of aqueous 5% NaHCO$_3$ solution was added a solution of 20.8 mg (0.11 mmol) of 2,4-dinitrofluorobenzene in 1 mL of 1,4-dioxane. The reaction mixture was allowed to ambient temperatures and stirred for overnight. The reaction mixture was diluted with 5 mL of water and extracted with two 10 mL portions of ethyl acetate. The organic phase was dried (MgSO$_4$) and concentrated under diminished pressure. The residue was purified by chromatography on a silica gel column (10×1 cm). Elution with 19:1 ethyl acetate/methanol gave desired product 4 as a pale yellow solid: yield 8.4 mg (24%); silica gel TLC R$_f$ 0.13 (19:1 ethyl acetate/methanol); $^1$H NMR (CDCl$_3$) δ 1.29-1.35 (m, 4H), 1.46 (s, 18H), 1.48-1.54 (m, 4H), 1.69 (m, 2H), 2.19 (d, 4H, J=6.8 Hz), 2.31 (t, 8H, J=4.4 Hz) and 3.44 (t, 8H, J=2.6 Hz), 7.64 (d, 2H, J=8.0 Hz), 8.40 (dd, 2H, J=9.2 Hz and 2.4 Hz) and 8.43 (d, 1H, J=2.8 Hz); $^{13}$C NMR (CDCl$_3$) δ 26.7, 31.8, 32.1, 53.3, 62.1, 117.2, 122.3, 129.3, 136.7, 141.5 and 154.3.

In Vitro Cellular Proliferation Assay: BT474 breast cancer cells (ATCC® HTB-20, overexpression of HER2), A549 lung cancer cells, leukemia cell CCRF-CEM (ATCC# CCL-119), and leukemia Jurkat cell were cultured at 37° C. in a 5% CO$_2$ atmosphere and grown in Gibco® RPMI 1640 medium supplemented with 10% fetal bovine serum (FBS) and 1% antibiotic-antimitotic mix antibiotic supplement before use.

Exponentially growing cells were harvested and plated in 96-well plates at a concentration of 1×10$^4$ cells/well. After incubation at 37° C. for 24 h, the cells were treated with analogues of JS-K at different concentrations for an additional 24, 48 or 72 h. Then 20 μL of MTT (5 mg/mL) or MTS was added to each well and the plates were incubated at 37° C. for 4 h. The supernatant was discarded for MTT assay, and 100 μL of DMSO was added to each well. For the MTS assay, this step is not necessary. The absorbance was recorded at 490 nm after 15 min. Inhibition of cell growth was obtained by the following formula: Inhibition of cell growth (%)=($OD_{negative\ control}$−$OD_{treatment}$)×100%/($OD_{negative\ control}$−$OD_{background}$). Data are reported as the mean of three independent experiments, each run in quintuplicate.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A compound selected from formula I:

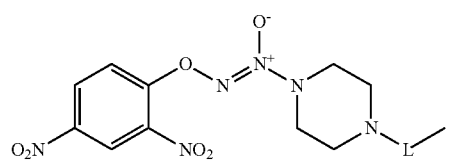

I

-continued

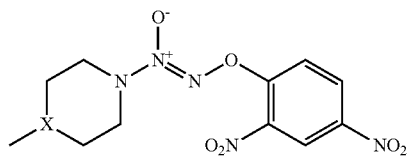

wherein:

X is CH or N; and

L is selected from $C_1$-$C_{10}$ alkyldiyl, $C_1$-$C_{10}$ alkyldiyl-($C_3$-$C_6$ cycloalkyldiyl), and $C_1$-$C_{10}$ alkyldiyl-($C_3$-$C_6$ cycloalkyldiyl)-$C_1$-$C_{10}$ alkyldiyl, where alkyldiyl and cycloalkyldiyl are independently and optionally substituted with one or more groups selected from halo, hydroxy, nitro, cyano, ($C_1$-$C_6$) alkoxy, and oxo (═O);

or a pharmaceutically-acceptable salt thereof.

2. The compound of claim 1 which is a compound of formulae Ia, Ib, or Ic:

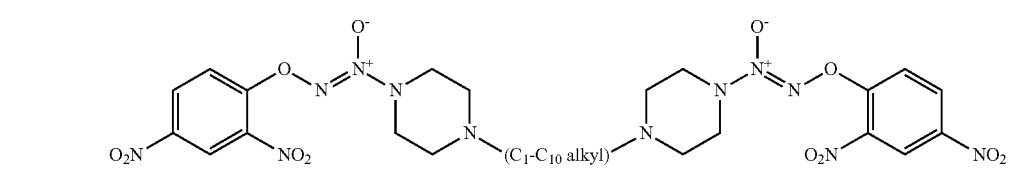

Ia

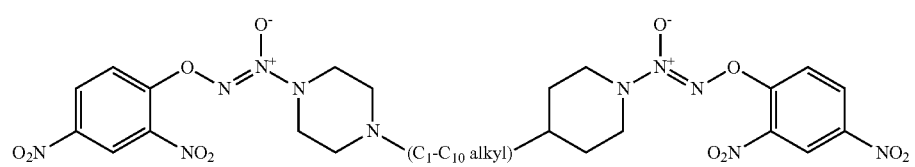

Ib

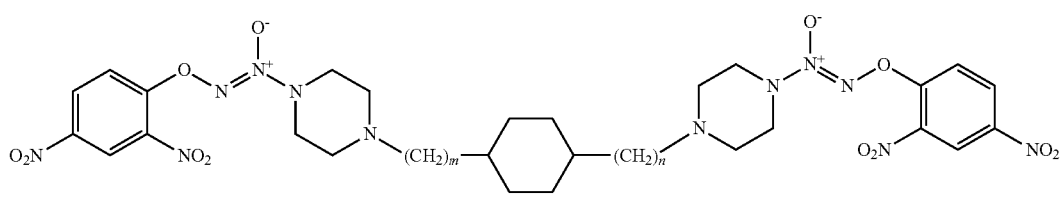

Ic where m and n are independently selected from 1, 2, and 3.

3. The compound of claim 1 wherein X is CH.

4. The compound of claim 1 wherein X is N.

5. The compound of claim 1 wherein L is optionally substituted $C_1$-$C_{10}$ alkyldiyl.

6. The compound of claim 1 wherein L is selected from —$CH_2$—, —$CH_2CH_2$—, and —$CH_2CH_2CH_2$—.

7. The compound of claim 1 wherein L is optionally substituted $C_1$-$C_{10}$ alkyldiyl-($C_3$-$C_6$ cycloalkyldiyl).

8. The compound of claim 1 wherein L is optionally substituted $C_1$-$C_{10}$ alkyldiyl-($C_3$-$C_6$ cycloalkyldiyl)-$C_1$-$C_{10}$ alkyldiyl.

9. A compound selected from compounds 1-4:

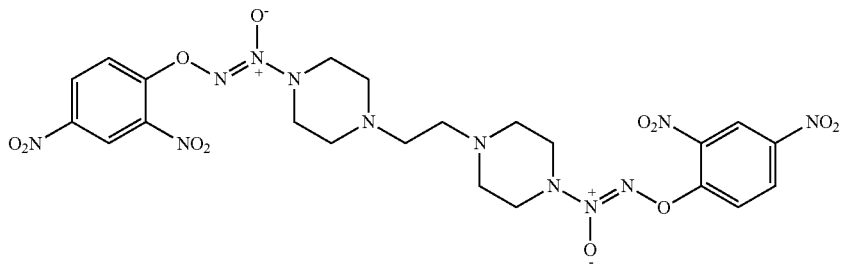

1

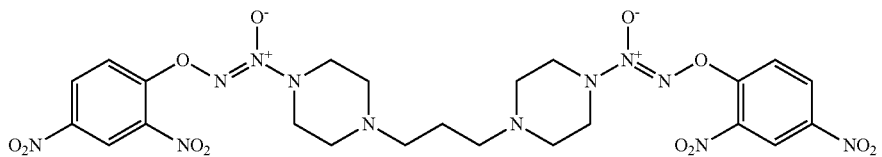

2

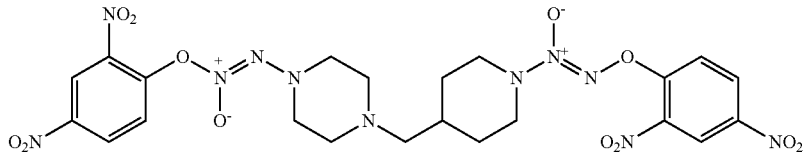

3

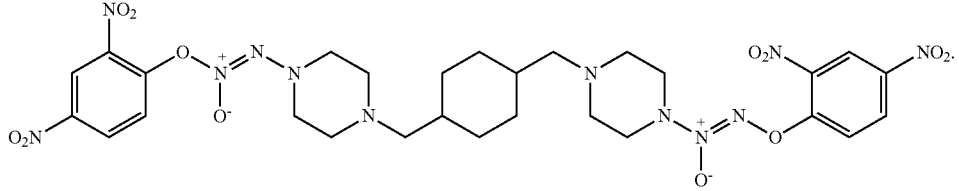

4

10. A pharmaceutical composition comprising a compound of formula I as described in claim 1, or a pharmaceutically acceptable salt thereof, and a pharmaceutically acceptable carrier, glidant, or excipient.

11. A method for treating cancer in an animal in need thereof, comprising administering a therapeutically-effective amount of a compound of formula I as described in claim 1, or a pharmaceutically acceptable salt thereof, to the said animal; wherein the cancer is selected from pancreatic cancer, bile duct carcinoma, neuroblastoma, colon cancer, breast cancer, myeloma, gastric cancer, liver cancer, gliblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.

12. The method of claim 11 wherein the cancer is breast cancer.

13. A method for inhibiting cancer cell growth in an animal in need thereof, comprising administering an inhibitory effective amount of a compound of formula I as described in claim 1, or a pharmaceutically acceptable salt thereof, to the said animal; wherein the cancer is selected from pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.

14. The method of claim 13 wherein the cancer cell is a breast cancer cell.

* * * * *